(12) United States Patent
Rosenfeld

(10) Patent No.: US 7,918,837 B2
(45) Date of Patent: Apr. 5, 2011

(54) BODY-ATTACHABLE SANITARY NAPKIN

(75) Inventor: Leonard G. Rosenfeld, Yardley, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 603 days.

(21) Appl. No.: 11/958,970

(22) Filed: Dec. 18, 2007

(65) Prior Publication Data

US 2009/0118691 A1    May 7, 2009

Related U.S. Application Data

(60) Provisional application No. 60/984,204, filed on Oct. 31, 2007.

(51) Int. Cl.
    *A61F 13/47* (2006.01)
(52) U.S. Cl. .................. 604/385.03; 604/387
(58) Field of Classification Search .......... 604/385.03–385.05, 385.22, 387
    See application file for complete search history.

(56) References Cited

U.S. PATENT DOCUMENTS

| | | | | |
|---|---|---|---|---|
| 2,512,713 A * | 6/1950 | Cahill | 604/390 |
| 2,742,903 A * | 4/1956 | Lightner | 604/387 |
| 3,906,952 A * | 9/1975 | Zamist | 604/372 |
| 4,072,151 A * | 2/1978 | Levine | 604/387 |
| 4,484,919 A * | 11/1984 | Sohn et al. | 604/358 |
| 4,753,648 A * | 6/1988 | Jackson | 604/389 |
| 5,114,419 A * | 5/1992 | Daniel et al. | 604/385.15 |
| 5,445,627 A * | 8/1995 | Mizutani et al. | 604/385.28 |
| 5,618,281 A * | 4/1997 | Betrabet et al. | 604/387 |
| 5,618,282 A * | 4/1997 | Schlangen | 604/387 |
| 5,658,270 A * | 8/1997 | Lichstein | 604/387 |
| 5,807,367 A * | 9/1998 | Dilnik et al. | 604/369 |
| 6,191,189 B1 * | 2/2001 | Cinelli et al. | 523/111 |
| 6,211,263 B1 * | 4/2001 | Cinelli et al. | 523/111 |
| 6,213,993 B1 * | 4/2001 | Zacharias et al. | 604/386 |
| 6,296,628 B1 * | 10/2001 | Mizutani | 604/387 |
| 6,365,645 B1 * | 4/2002 | Cinelli et al. | 523/105 |
| 6,620,143 B1 * | 9/2003 | Zacharias et al. | 604/385.03 |
| 6,824,535 B2 * | 11/2004 | Kolby-Falk | 604/385.03 |
| 7,033,342 B2 * | 4/2006 | Mizutani et al. | 604/385.02 |
| 7,122,022 B2 * | 10/2006 | Drevik | 604/385.03 |
| 7,125,401 B2 * | 10/2006 | Yoshimasa | 604/392 |
| 7,578,810 B2 * | 8/2009 | Rosenfeld et al. | 604/385.01 |
| 7,611,501 B2 * | 11/2009 | Luizzi | 604/385.03 |
| 2002/0013566 A1 * | 1/2002 | Chappell et al. | 604/385.13 |
| 2002/0120247 A1 * | 8/2002 | Mizutani et al. | 604/385.17 |
| 2003/0078554 A1 * | 4/2003 | Drevik | 604/385.03 |
| 2003/0135188 A1 * | 7/2003 | Yoshimasa | 604/385.03 |
| 2003/0163108 A1 * | 8/2003 | Tears et al. | 604/385.03 |
| 2004/0158221 A1 * | 8/2004 | Mizutani et al. | 604/385.17 |
| 2004/0254554 A1 | 12/2004 | Mavinkurve et al. | |
| 2005/0148981 A1 * | 7/2005 | Price et al. | 604/385.03 |
| 2006/0058760 A1 * | 3/2006 | Rosenfeld et al. | 604/380 |

(Continued)

FOREIGN PATENT DOCUMENTS

EP        336578 A    10/1989

(Continued)

*Primary Examiner* — Tatyana Zalukaeva
*Assistant Examiner* — Paula L Craig

(57) ABSTRACT

A body-attachable sanitary napkin including a fluid-pervious cover layer, a fluid-retaining assembly; and a barrier layer having a body-contactable adhesive disposed on at least first portions thereof. The sanitary napkin according to the invention remains securely attached to the body during use, moves with the body during use, yet at the same time enables the user to selectively remove the napkin in a pain free manner.

7 Claims, 5 Drawing Sheets

U.S. PATENT DOCUMENTS

2006/0142722 A1* 6/2006 Koenig et al. ............ 604/385.03
2006/0224134 A1* 10/2006 Luizzi et al. ............. 604/385.05
2007/0100313 A1* 5/2007 Luizzi ........................ 604/389
2007/0287973 A1* 12/2007 Cohen et al. ............. 604/385.03
2009/0036858 A1* 2/2009 Van Den Bogart
 et al. ........................ 604/385.03
2009/0118692 A1* 5/2009 Rosenfeld ................ 604/385.03

FOREIGN PATENT DOCUMENTS

| EP | 847737 A | 6/1998 |
| EP | 1637109 A | 3/2006 |
| EP | 1779828 A | 5/2007 |
| WO | WO 96/13238 A | 5/1996 |
| WO | WO 2005/099645 A | 10/2005 |

* cited by examiner

BODY-ATTACHABLE SANITARY NAPKIN

CROSS REFERENCE TO RELATED APPLICATIONS

This application claims priority to Application No. 60/984,204 filed on Oct. 31, 2007, the entire contents of which are incorporated by reference herein.

FIELD OF THE INVENTION

The present invention generally relates to sanitary absorbent articles and in particular to sanitary napkins that are directly attachable to the body.

BACKGROUND OF THE INVENTION

Externally worn, sanitary napkins are one of many kinds of feminine protection devices currently available. In use, the typical sanitary napkin is positioned in the perineal region to capture bodily discharge, e.g., menses. In order to prevent the sanitary napkin from drifting into a position that would compromise the sanitary napkin's ability to manage bodily discharges, the sanitary napkin is generally affixed to a user's undergarment, most commonly with adhesive that is applied to a garment facing surface of the sanitary napkin. The adhesive essentially joins the sanitary napkin to the user's underwear.

An alternative sanitary napkin design, the so-called, "body-attachable" sanitary napkin, includes a means for affixing the sanitary napkin directly to the user's body, typically using a body-contactable adhesive. For example, U.S. Pat. No. 6,213,993 purports to disclose a self-adhering absorbent article including a liquid-permeable cover, an absorbent core, a liquid impermeable baffle, and a bodyside adhesive arranged on the cover for securing the article to the body.

Unfortunately, it is difficult to design a body-attachable sanitary napkin that will remain attached to the user in a manner that is comfortable to the user and sufficient to prevent leakage. Applicants have recognized that conventional body-attachable sanitary napkins do not move sufficiently with the body during either resulting in leakage and/or detachment from the body. Applicants have further recognized that conventional body-attachable sanitary napkins do not remain securely attached to the body during use, move with the body during use, yet at the same time enable the user to selectively remove the napkin in a pain free manner. As such, a need exists to overcome one or more of the above-mentioned drawbacks.

SUMMARY OF THE INVENTION

According to a first aspect of the invention, the present invention provides a body-attachable sanitary napkin, comprising: an extensible barrier layer having a first portion and a second portion, said second portion having a body-attachable adhesive arranged thereon; and a fluid-retaining assembly arranged in overlapping relationship to said first portion of said barrier layer thereby defining an area of juxtaposition between said fluid-retaining assembly and said barrier layer, and wherein said fluid-retaining assembly is secured to said barrier layer along a selected portion of said area of juxtaposition.

BRIEF DESCRIPTION OF THE DRAWINGS

Examples of embodiments of the present invention will now be described with reference to the drawings, in which.

DETAILED DESCRIPTION OF THE INVENTION

The present invention provides a body-attachable sanitary napkin that is generally able to accommodate the demands of moving with the body, remaining attached thereto in use, while permitting the fluid-retaining assembly to remain positioned to receive and retain bodily fluid. As such, the sanitary napkin includes, in certain embodiments, a fluid-retaining assembly that is secured to a barrier layer only along selected portions of an area of juxtaposition between the fluid-retaining assembly and the barrier. By including a fluid-retaining assembly that has reduced securement to the barrier layer, the demands that would otherwise be placed on either the barrier layer or adhesive, or both, is greatly reduced.

Applicants have further determined that a body-attachable sanitary napkin can overcome the challenge of simultaneously providing both high stay in place as well as reduced removal pain by selecting the barrier layer, selecting the body-contactable adhesive and arranging the sanitary napkin, all in a certain manner. In particular, Applicants have provided herein a sanitary napkin construction that remains securely attached to the body during use, moves with the body during use, yet also enables the user to selectively remove the napkin in a pain free manner.

The peel force values described herein are affected by both the nature of the body-contactable adhesive as well as the selection of the barrier layer. The criticality of the results of Applicant's PEEL FORCE TEST PROCEDURE as well as the combination of this criticality combined with the criticality of the results of Applicant's PEAK FORCE-20% STRETCH TEST PROCEDURE has not previously been identified as useful parameters in the design of body-attachable sanitary napkins.

By designing the body-contactable sanitary napkin to meet the requirements above, it is possible to include a wider range of barrier materials, a wider range of adhesives, and/or a wider variety of designs than were suggested in the prior art.

Figure 1:
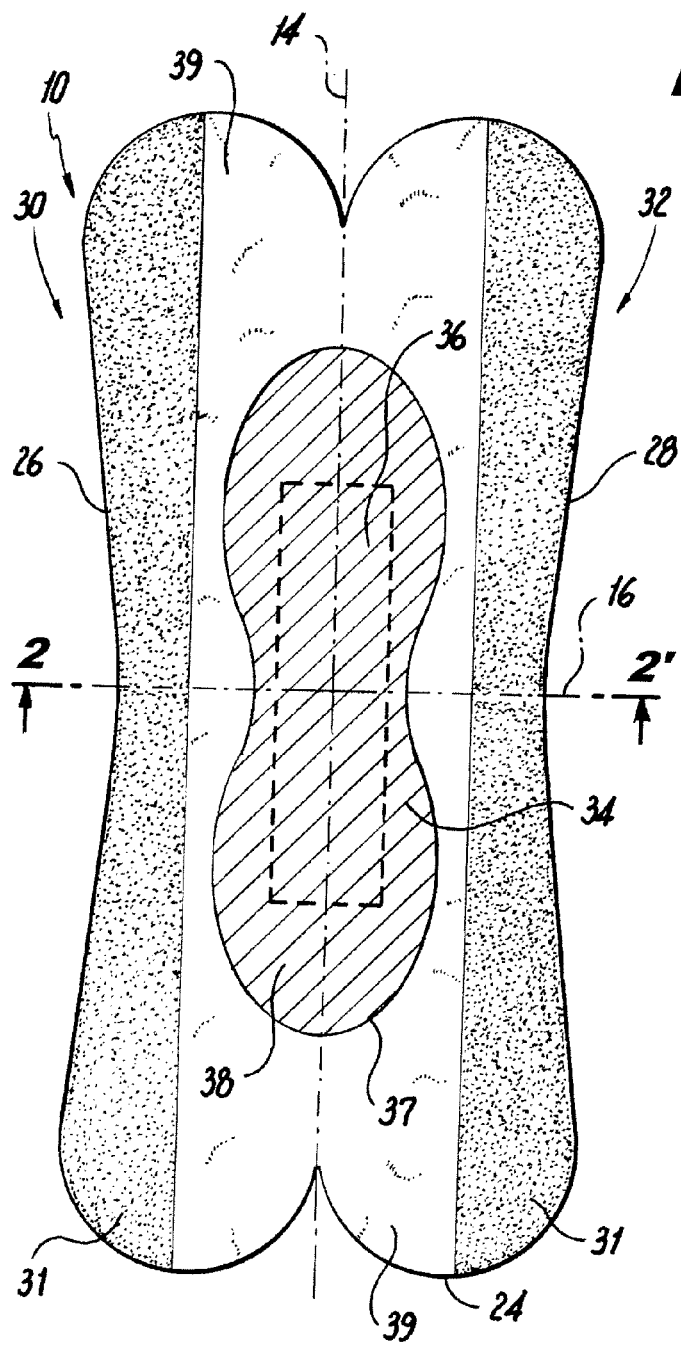
FIG. 1 is a top plan view of a sanitary napkin in accordance with a first embodiment of the present invention.
Figure 2:
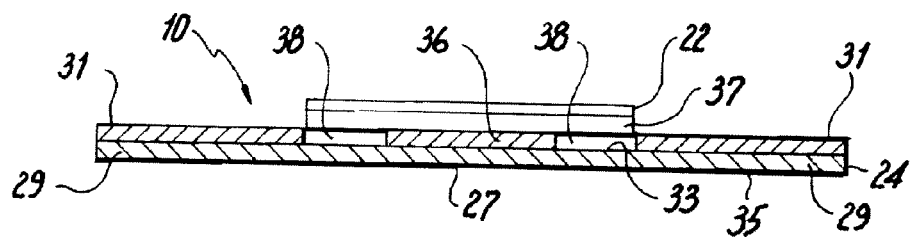
FIG. 2 is a sectional view of the sanitary napkin of FIG. 1, taken through the transverse centerline, line 2-2' thereof.

Referring to FIGS. 1-2, there is shown a first embodiment of the present invention, a feminine sanitary napkin 10. FIG. 1 depicts a top plan view of the sanitary napkin shown in FIG. 1. The sanitary napkin 10 a first transverse side 26 defining a front portion thereof and a second transverse side 28 defining a rear portion thereof. The sanitary napkin 10 also has two longitudinal sides, namely a first longitudinal side 30 and a second longitudinal side 32.

The sanitary napkin 10 has a longitudinal centerline 14 that bisects the sanitary napkin 10 in two identical halves and an imaginary transverse centerline 16 arranged perpendicular to the longitudinal centerline 14. FIG. 2 depicts a cross-sectional view of the sanitary napkin shown in FIG. 1, taken through line 2-2'.

As shown in FIGS. 1-2, sanitary napkin 10 is of a laminate construction and comprises an extensible barrier layer 24. The extensible barrier layer 24 has a top face 33 that generally faces the body of the user and a bottom face 35 that generally faces the user's undergarment.

A fluid-retaining assembly 37 is arranged in overlapping relationship to a first portion 27 of the extensible barrier layer 24, thereby defining an area of juxtaposition 34 between the fluid-retaining assembly 37 and the extensible barrier layer 24. The first portion 27 of the extensible barrier layer 24, the fluid-retaining assembly 37, and the area of juxtaposition 34 defined by the overlapping of these components are depicted in FIG. 1 as the "peanut-shaped," cross-hatched region. The first portion 27 of the extensible barrier layer 24, since it is overlapped by the fluid-retaining assembly, does not include a skin-contactable surface.

The extensible barrier layer 24 further includes a second portion 29 that extends outwardly beyond the first portion. The body-contactable adhesive 31 is formed upon the top face 33 of the second portion 29 of the extensible barrier layer 24.

The extensible barrier layer 24 may also include a third portion 39. The third portion 39 is outside the area of juxtaposition 34. As such it is body-contactable. However, the third portion 39 includes no body-contactable adhesive formed thereon.

The shape of the extensible barrier layer 24 is variable and may be designed to facilitate skin contact with skin along the groin/inner thigh. Furthermore, the shape of the fluid-retaining assembly 37 is variable and may be selected to facilitate coverage of the perineal region of the user. As a percent of the total area of the extensible barrier layer 24 when laid flat (i.e., the "footprint" of the extensible barrier layer 24—as shown in FIG. 1), the area of the fluid retaining portion 37 may be from about 10% to about 90%, preferably from about 40% to about 80%.

The shape of the second portion 29 of the extensible barrier layer 24 is also variable and may be designed to facilitate contact with the user and may be further designed for ease of manufacture. As depicted in FIG. 1, the shape of second portion 29 may include or consist essentially of one or more longitudinally-oriented stripes on either side of longitudinal centerline 14. Other configurations, e.g., one or more squares, rectangles, circles, dotted stripes, strips, swirls, or waves are also contemplated.

The fluid-retaining assembly 37 is secured to the first portion 27 of the extensible barrier layer 24 along a selected portion 36 (the outline of which is shown as a rectangularly-shaped area in phantom in FIG. 1) of the area of juxtaposition 34. Along non-selected portions 38 (depicted in FIG. 1 as that portion of the "peanut-shaped" area of juxtaposition 34 that is outside the rectangular-shaped selected portion 36), the fluid-retaining assembly 37 is not secured to the first portion 27 of the extensible barrier layer 24. By "secured" it is meant that selected portion 36 the extensible barrier layer 24 and the fluid-retaining portion 37 are either directly or indirectly connected and are designed to remain connected in use.

The selected portion 36 as a fraction of the area of juxtaposition 34 is not so low as to allow the fluid-retaining assembly 37 to move too freely and/or risk detachment from the sanitary napkin 10, yet it is not so large that motion is unnecessarily restricted. In one embodiment of the invention, the selected portion is from about 5% to about 90% of the area of juxtaposition 34, preferably from about 20% to about 80%, more preferably from about 30% to about 70%.

Figure 3:
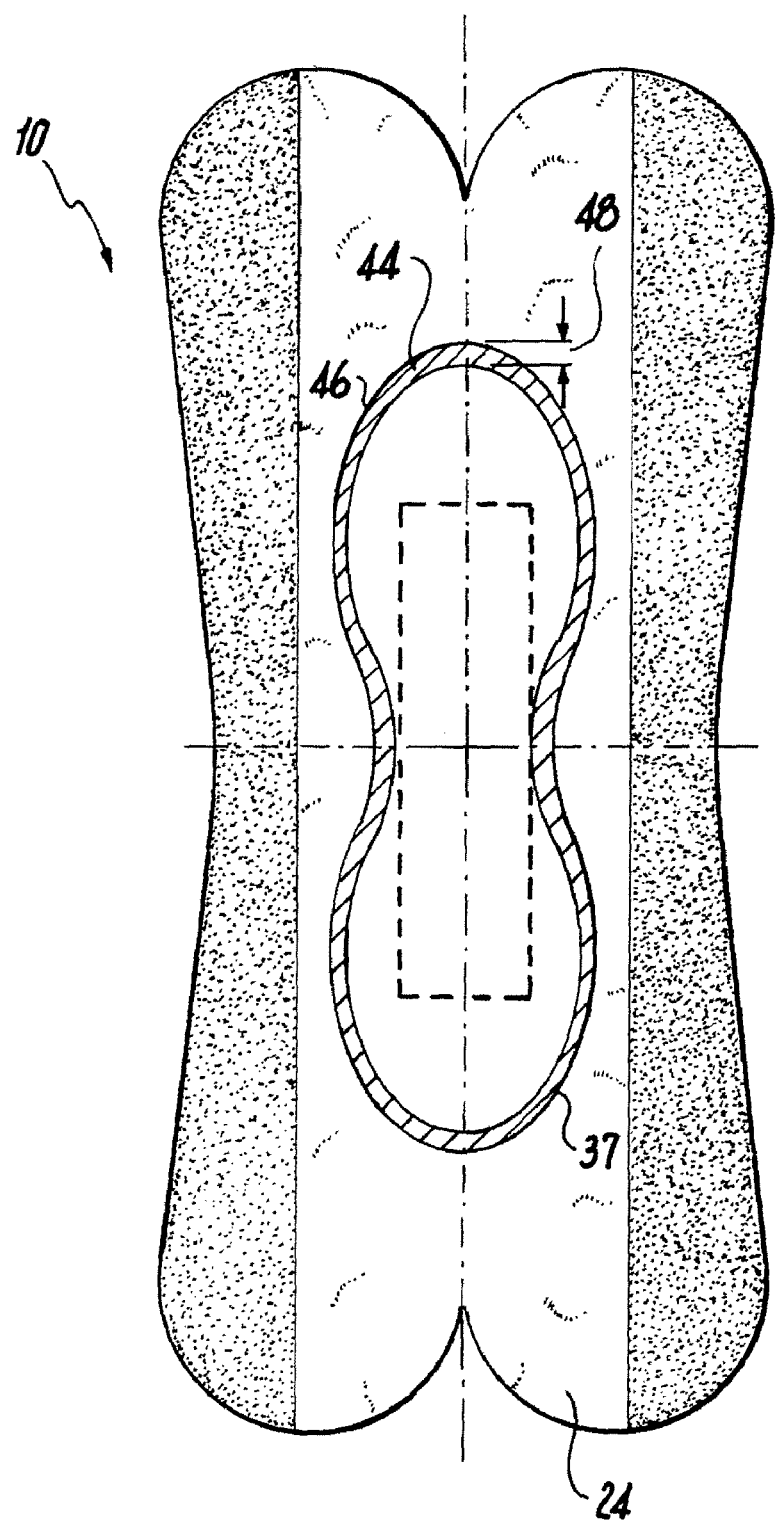
FIG. 3 is a top plan view of a sanitary napkin of FIG. 1, showing additional features thereof.

FIG. 3 is top plan view of the sanitary napkin of FIG. 1, showing additional features thereof. As shown in FIG. 3, the overlapping of the fluid-retaining assembly 37 with the extensible barrier layer 24 further defines a perimeter 46 of juxtaposition, an imaginary shape that bounds the fluid-retaining portion 37. The perimeter 46 of juxtaposition defines a peripheral region of juxtaposition 44, that portion of the area of juxtaposition 34 along the perimeter 46 of juxtaposition and having a constant width 48, such that the peripheral region of juxtaposition 44 accounts for 10% of the total area of juxtaposition 34. In one embodiment of the invention, at least about 50% of the peripheral region of juxtaposition is not secured to the extensible barrier layer 24. In a preferred embodiment, greater 75% of the peripheral region of juxtaposition is not so secured.

Figure 4:
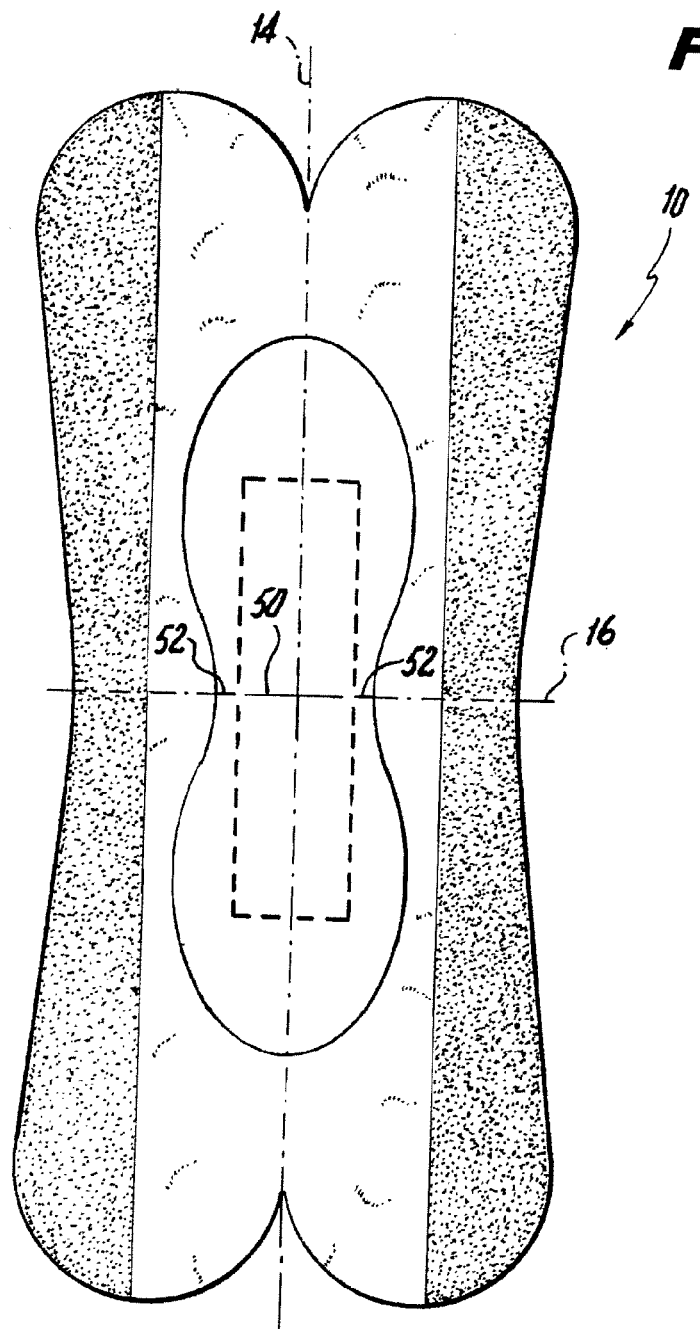
FIG. 4 is a top plan view of a sanitary napkin of FIG. 1, showing yet additional features thereof.

FIG. 4 is top plan view of the sanitary napkin of FIG. 1, showing yet additional features thereof. As shown in FIG. 3, the overlapping of the fluid-retaining assembly 37 with the extensible barrier layer 24 further defines one or more segments of attachment 50, e.g., segments of the transverse centerline 16 within the area of juxtaposition 34 that are secured to the extensible barrier layer 24 (shown in phantom in FIG. 4) and one or more segments of unattachment 52; e.g., a segment of the transverse centerline 16 within the area of juxtaposition 34 that are not secured to the extensible barrier layer 24 (shown as a solid line in FIG. 4. In one embodiment, the total length of the segments of unattachment 52 are greater than about 15% of that of the total length of the segments of attachment 50. In a preferred embodiment, the length of the segment of unattachment 52 is greater than about 30% of that of the length of the segments of attachment 50. While in FIG. 4, the line from which the segments of attachment 50 and segments of unattachment 52 is the transverse centerline 16, the longitudinal centerline 14 or a line at any angle in between the transverse centerline 16 and the longitudinal centerline could be used to determine suitable segments of attachment of unattachment.

While FIGS. 1, 3 and 4 depict the shape of the selected portion 36 of the area of juxtaposition 34 to be a single continuous rectangular area, other shapes for the selected portion 36 are contemplated. For example, the selected portion 36 may include one or more areas of squares, rectangles, circles, dotted stripes, strips, swirls, or waves etc. and may include or not include the center (intersection of the longitudinal centerline 14 and transverse center line 16).

Figure 5:
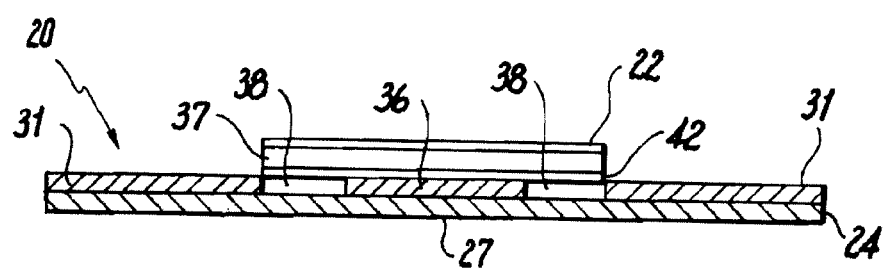
FIG. 5 is cross-sectional view of a sanitary napkin sanitary napkin in accordance with a second embodiment of the present invention.

FIG. 5 depicts an alternative embodiment of the invention of a sanitary napkin 20. Sanitary napkin 20 is identical to the sanitary napkin 10 of FIGS. 1-2, except that sanitary napkin 20 includes an additional fluid-impervious barrier layer 42, distinct from the extensible barrier layer 24. Additional barrier layer 42 is positioned intermediate (e.g., between) the fluid-retaining assembly 37 and the extensible barrier layer 24. As such, the additional barrier layer 42 provides additional ability to trap bodily fluids and prevent leakage of fluid outside the sanitary napkin 20. In one embodiment, the additional barrier layer 42 is sized to just accommodate the fluid-retaining assembly 37 and, as such, the additional barrier layer 42 does not extend beyond the area of juxtaposition 34 and is free of the body-contactable adhesive 31.

Barrier Layer

The extensible barrier layer 24 is generally liquid impervious. By "liquid impervious" it is meant that liquids such as menses and urine, under in-use conditions are unable to pass through. By "extensible", it is meant that when placed under tension in the plane of the layer, the extensible barrier layer 24 can stretch (elastically) 10% or more, preferably 20% or more and essentially recover its original length. The extensible barrier layer 24 may include, for example, polymeric film such as polyethylene or polypropylene; liquid impervious (e.g., repellent-treated) non-wovens (e.g., spunbond, melt-blown, or thermobonded polyolefin or polyurethane fibers that have been treated to prevent the penetration of bodily fluids therethrough; or combinations or laminates thereof. The extensible barrier layer 24 may have a basis weight from about 5 gsm to about 20 gsm. Notable liquid impervious extensible barrier films include spunbond liquid-impervious nonwovens of polyurethane and/or polypropylene; with or without layers of meltblown fibers arranged in between.

The extensible barrier layer 24 may be breathable, i.e., permits vapor to transpire. Known materials for this purpose include nonwoven materials and microporous films in which microporosity is created by, inter alia, placing the extensible barrier layer 24 in tension. Single or multiple layers of permeable films, fabrics, melt-blown materials, and combinations thereof that provide a tortuous path, and/or whose surface characteristics provide a liquid surface repellent to the penetration of liquids may also be used to provide a breathable barrier layer.

Optional additional barrier layer 42, as shown in FIG. 4 may be of similar composition and generally has similar liquid-imperviousness as described above for the extensible barrier layer 24.

Body-Contactable Adhesive

The body-contactable adhesive 31 is formed on a body-faceable side of the extensible barrier layer 24 for securing the sanitary napkin 10 to the body of a user, during use. The body-contactable adhesive 31 may be covered with removable release paper so that the body-contactable adhesive 31 is covered by the removable release paper prior to use.

The body-contactable adhesive 31 may include pressure sensitive adhesive and may be applied in various suitable configurations as previously described. As used herein, the term pressure-sensitive adhesive refers to any releasable adhesive or releasable tenacious means.

The composition of the body-contactable adhesive 31 is variable, as long as the adhesive is selected such that when the sanitary napkin is tested according to the test methods described herein, both (1) a suitable force to effect peeling of the adhesive and (2) a low enough force to effect a particular 20% stretch when subject to tension across the sanitary napkin.

The body-contactable adhesive 31 used in sanitary napkin may be an adhesive based upon block copolymers such as those which may include linear or radial co-polymer structures having the formula $(A-B)_x$ wherein block A is a polyvinylarene block, block B is a poly(monoalkenyl) block, x denotes the number of polymeric arms, and wherein x is an integer greater than or equal to one. Suitable block A polyvinylarenes include, but are not limited to polystyrene, polyalpha-methylstyrene, polyvinyltoluene, and combinations thereof. Suitable Block B poly(monoalkenyl) blocks include, but are not limited to conjugated diene elastomers such as for example polybutadiene or polyisoprene or most preferably hydrogenated elastomers such as ethylene-butylene or ethylene-propylene or polyisobutylene, or combinations thereof, specifically, adhesives consisting of styrene-ethylene-butylene-styrene (SEBS) block copolymer and mineral oils, paraffinic or napthenic process oils, and optionally a suitable tackifying resins include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof, aromatic petroleum resin and the hydrogenated derivatives thereof; and aliphatic/aromatic petroleum resins and the hydrogenated derivatives thereof, and combinations thereof.

The body-contactable adhesive 31 employed in the article according to the present invention may have more than about 50% by weight of a liquid plasticizer, such as more than about 65% by weight of a liquid plasticizer. Suitable liquid plasticizers may include white oils, mineral oils, paraffinic process oils, polyethylene glycol, glycerin, polypropylene glycol, napthenic oils, and liquid polyterpenes. The liquid plasticizer preferably has a molecular weight of less than 1000 g/mole, more preferably less than 750 g/mole and most preferably less than 500 g/mole.

The body-contactable adhesive 31 may be of the type described in U.S. Pat. No. 6,191,189 to Cinelli et al. In particular, the adhesive may comprise:

from 0.5 to 20%, preferably 5% to 15%, by weight of a macromolecular polymeric substance or a mixture of such substances soluble or swellable in the below mentioned plasticiser(s). As not limiting examples such macromolecular or polymeric substances can be natural and/or synthetic such as natural gums or derivatives such as natural gums and gelatins, their derivatives and alginates; polyacrylics; polyvinyl alcohol; polyethylene oxide; polyvinylpyrrolidone (PVP) or polyvinylethers, their copolymers and derivatives; cellulose derivatives; Block Copolymer Thermoplastic Elastomers and preferably Styrenic Block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS);

from 45 to 99.5% by weight, preferably from 51 to 99.5% by weight, of a plasticising substance or a mixture of plasticising substances, which are liquid at room temperature. As non-limiting examples the plasticiser can be water, various alcohols (like in particular glycerol), glycols and their ethers, polyglycols, liquid polybutenes, esters such phthalates, adipates, stearates, palmitates, sebacates, or myristates, natural or synthetic oils such as vegetable oils, mineral oils, or combinations thereof;

from 0% to 50% by weight of the composition, preferably from 0 to 600% by weight of the macromolecular polymeric substance of a tackifying resin whose main scope is to tailor the Tg especially in systems based on synthetic polymers;

from 0 to 10% and more preferably form 0 to 5% by weight of substances for facilitating and stabilising the gel and the gel forming process both of hydrophilic or hydrophobic liquid plasticisers. These may be for oily systems, e.g. the fatty acids of $C_8$ to $C_{22}$, their metallic salts and their polyoxo-derivatives; lanolin derivatives; silica; bentonite, montmorillonite and their derivatives; polyamides, waxes or mixtures thereof.

The adhesive may also be of the type described U.S. Pat. No. 6,213,993 to Zacharias et al. In particular the adhesive may comprise:

a rubber-based adhesive such as styrenebutadiene, polyisobutylene, polybutadiene and polyisoprene; a water soluble adhesive such as polyvinyl alcohol, polyvinyl acetate, and methyl cellulose; a hot melt adhesive such as block copolymers of styrene-butadiene-styrene, styrene-isoprene-styrene, styrene-ethylenepropylene-styrene, styrene-ethylenebutylene-styrene and tetrablock copolymers such as styrene-ethylenepropylene-styrene-ethylenepropylene. Incorporated with the adhesives can be suitable tackifying resins and, if appropriate, oils.

Other adhesive types here include anhydrous gels consisting of 2-hydroxyethyl methacrylate polymer, polyethylene glycol and optionally water as taught in U.S. Pat. No. 4,303,066 and polyurethane gels, as disclosed in USA U.S. Pat. No. 4,661,099, or silicone gels including commercial products such as Silgel 612 from Wacker Silicones (Adrian, Mich.) or SSA-9700 Soft Skin Adhesives Dow-Corning (Midland, Mich.).

Other suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof, hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include KRATON elastomers from Shell Chemical Company, VECTOR elastomers from Dexco, Solprene™ from Enichem Elastomers and STEREON from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Fluid-Retaining Assembly

Sanitary napkins of the present invention include fluid retaining assembly 37. As used herein, the term "fluid-retaining assembly" refers to any material or multiple material layers whose primary function is to absorb, store or distribute fluid especially menses that is discharged by the wearer and prevent the back flow of stored fluid towards the cover and contacting the wearer.

The fluid retaining assembly 37 may include a single layer of material or may include multiple layers (e.g., an absorbent core overlayed by a so-called "transfer," "distribution" or "acquisition" layer). In one embodiment, fluid-retaining assembly 37 is a blend or mixture of cellulosic fibers and superabsorbent disposed in and amongst fibers of that pulp.

It is possible that the fluid-retaining assembly 37 could be integrated with the cover and/or barrier such that there is essentially only a single layer structure or a two layer structure including the function of the multiple layers described herein.

Cellulosic fibers that can be used in the fluid-retaining assembly 37 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material. The fluid-retaining assembly 37 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

The fluid-retaining assembly 37 may comprise a material manufactured by using air-laying means well known in the art. In a specific example, the fluid-retaining assembly 37 is an air laid material made from cellulosic fibers, bonding materials and components that cannot form a bond (nonbonding materials) with the other component materials.

In one specific embodiment of the invention, the absorbent system is composed of fluff pulp.

Attachment of Fluid-Retaining Assembly to Barrier Layer

In certain embodiments of the invention, the fluid retaining assembly 37 is secured to the extensible barrier layer 24 along a selected portion 36 of the area of juxtaposition 34. The securement may be made by means of construction adhesives, heat-bonding, ultrasonic bonding, radio frequency sealing, mechanical crimping, or similar techniques known to the art of joining fibrous and/or film materials for use in absorbent articles.

In one embodiment, the selected portion 36 is secured using a construction adhesive. Suitable construction adhesives include, for example, hot melt adhesives, such are those that are sufficiently pressure sensitive at elevated (application) temperatures and have sufficient cohesive and peel strength at ambient temperatures to maintain a firm bond the selected portion 36 of the barrier layer to the fluid-retaining portion 37 while the sanitary napkin is in use. The construction adhesive may include block copolymers, plasticizers and/or reinforcing or tackifying resins.

Cover Layer

The sanitary napkin 10 may include cover layer 22. Cover layer 22 may include non-woven web material, an apertured thermoplastic film (such as those described in U.S. Pat. No. 4,690,679), or combinations thereof. The cover layer 22 may be composed of only one type of fiber, such as polyester or polypropylene or it may include a mixture of more than one fiber. The cover layer 22 may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 22 has a basis weight in the range of about 10 gsm to about 75 gsm.

Bi-component fibers suitable for use in cover layer 22 may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer 22 may be mounted to the absorbent layer and/or to the barrier layer.

The cover material should preferably contain a significant amount of relatively large pores or apertures. This is because the cover layer 22 is intended to take-up body fluid rapidly and transport it away from the body and the point of deposition. Therefore, the cover layer 22 contributes little to the time taken for the napkin to absorb a given quantity of liquid (penetration time).

Advantageously, the fibers which make up the layer 22 should not lose their physical properties when they are wetted, in other words they should not collapse or lose their resiliency when subjected to water or body fluid. The cover layer 22 may be treated to allow fluid to pass through it readily. The cover layer 22 also functions to transfer the fluid quickly to the other layers of the absorbent system 44. Thus, the cover layer 22 is advantageously wettable, hydrophilic and porous. When composed of synthetic hydrophobic fibers such as polyester or bi-component fibers, the cover layer 22 may be treated with a surfactant to impart the desired degree of wettability.

The fibers of the nonwoven cover may be bonded by any of various means such as spunlacing (hydroentanglement), thermobonding, latex bonding, and the like.

The cover layer 22 may be embossed to the fluid-retaining assembly 37 in order to aid in promoting hydrophilicity by fusing the cover layer 22 to the next layer. Such fusion may be effected locally, at a plurality of sites or over the entire contact surface of cover layer 22 and absorbent system 44. Alternatively, the cover layer 22 may be attached to the fluid-retaining assembly 37 by other means such as by adhesion.

Other Structures and Attributes

Sanitary napkins according to the present invention are preferably thin, preferably having a thickness of less than 4.0 mm, more preferably less than 3.0 mm, and most preferably less than 2.5 mm.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

While overall shape of the sanitary napkin may be symmetrical as shown in the Figures, it is also contemplated herein include asymmetrical and symmetrical absorbent articles having parallel longitudinal edges, dog bone- or peanut-shaped, as well as articles having a tapered construction for use with thong-style undergarments.

The sanitary napkin of the present invention may be applied to the crotch by placing the body-contactable adhesive against the inner thigh region of the user, thereby securing the absorbent assembly against the perineal region.

Test Procedures for Sanitary Articles: Procedures for Measuring (1) Peel Force and (2) Peak Force for 20% Stretch of the Body-Attachable Sanitary Napkin According to certain one aspect of the invention, in order to provide both reduced pain as well as improved stay in place, the body-attachable sanitary napkin has a Peel Energy, $G_c$ and a Young's modulus, E that satisfy the following relationship:

$$G/tE > 0.1 \text{ N/m; and}$$

$$tGE < 2 \times 10^5 \text{ N}^2/\text{m}^2$$

G/tE is a measure of the body-faceable sanitary napkin's ability to stay in place. It is calculated using "Peel Force," P, which is in turn determined using the PEEL FORCE TEST PROCEDURE. tGE is a measure of the sanitary napkin's ability to be peeled from the body with reduced pain. It is calculated using results from the PEEL FORCE TEST PROCEDURE as well as the "Peak Force at 20% Stretch," F, the latter of which is determined using the PEAK FORCE-20% STRETCH TEST PROCEDURE. The PEEL FORCE TEST PROCEDURE and the PEAK FORCE-20% STRETCH TEST PROCEDURE are each set forth in detail below.

"Peel Force" is determined by a test performed as follows. The PEEL FORCE TEST PROCEDURE is a measure of the force required to peel an adhesive from a standard sheet of plastic film. The apparatus necessary for the PEEL FORCE TEST PROCEDURE includes the following parts:

(1) A force-measurement gauge and more specifically an Instron inverted tension load cell. Instron Universal testing machine with load cell capable of measuring tensile forces from 10 to 200 grams (2000 gram capacity preferred), such as an Instron machine, e.g., Instron 1122 or 1125, commercially available from Instron Engineering Corporation, Canton, Mass.

(2) 90 degree peel fixture such as Instron 2820-035 or 2820-036.

(3) a grip attachable to force measurement gauge and suitable for pulling 1 cm peel strip without slip or tearing (e.g., 1½"×1" rubber face jaw plates)

(4) 2.5" by 7" pieces of double stick tape, e.g., PERMACEL available from Permacel, A Nitto Denko Company of East Brunswick, N.J.

(5) Rigid plastic or metal plate for clamping in peel fixture and attaching double stick tape and napkin sections. Approximately 3" by 7".

(6) 1 cm wide by 12" long sections of polyolefin film (hereinafter, "film adherent"), e.g., Pliant #3471 0.7 mil white polypropylene film.

Figure 6:
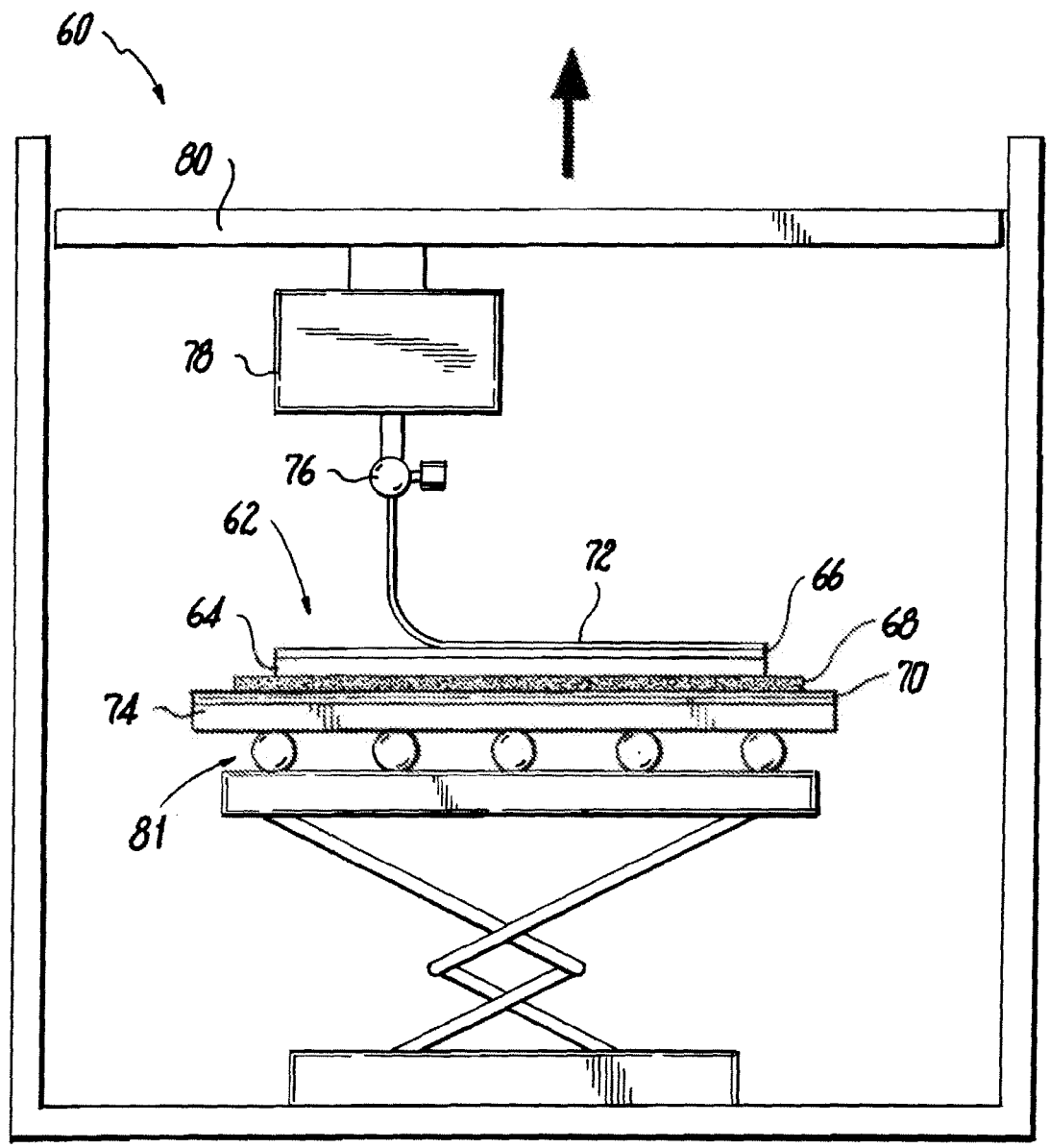
FIG. 6 is a schematic side view of a test apparatus suitable for conducting test procedures described herein on body-attachable sanitary napkins.

FIG. 6 depicts a schematic side view of an apparatus 60 suitable for the PEEL FORCE TEST PROCEDURE. Body adhesive should be protected from the environment until shortly before testing by a release liner or similar cover. A sample of the body adhesive section of the napkin is cut out to form test sample 62. Test sample 62 should be at least 1 cm wide and preferably 6" in length. If no such continuous region of body-faceable adhesive exists, then one should choose a 1 cm wide and 6" long portion that encompasses the greatest amount of body-contactable adhesive as possible. The layer of material in touch with the body adhesive is left intact but lower layers are removed so that the test sample is as flat as possible. The remaining test sample thus includes a substrate 64 and body-contactable adhesive 66 The double stick tape 68 is adhered to rigid plate 70 such that the body-faceable adhesive 66 is facing up. Any release liner is removed and the film adherent 72 is placed over the sample of body adhesive with the long end toward the screw clamp. A 1" square piece of release paper (if no release paper was provided with the test sample, any suitable release strip may be used) is placed at the point where the 1 cm sample turns up 90°, this will be the starting point of the test. The adherent film 72 is covered with release paper and rolled once with a 5 Lb. weight. The release film is then removed. The rigid plate 70 is firmly attached to the stage 74. The instron grip 76 is attached to the end of the film adherent 72 with the square piece of release paper, which is in turn are rigidly attached to moveable crosshead 80 of the Instron.

Tension cell 78 is allowed to warm-up 20 minutes before starting the calibration procedure. The load cell is calibrated once before any tests are done on a given day. Calibration is performed as per the manufacturers instructions, by attaching a standard 100 gram mass directly to the load cell.

The stage 74 is such that it capable of sliding with little friction in a direction normal with respect to the crosshead 80, thus allowing the film to be peeled from the adhesive at a continuous 90 degree angle. As such it may include roller 81 in order to reduce friction. The crosshead speed is set to 10.00 In/Min.

The force measurement apparatus records the force as the film adherent 72 is peeled (pulled up) from the rigid plate to which the body adhesive is attached. The measured peel force is recorded as the time averaged force from a section of the xy recording where stable peeling occurs. As readily determined by one skilled in the art, by "stable peeling" it is meant that time period of the force measurement can clearly be delineated as the onset and completion of peeling.

This average peel force, P is then be utilized to calculate Peel Energy, $G_c$ of the body adhesive, as set forth using the calculation below:

$$G_c = \{P^2/(2AEw)\} + \{P/(1-\cos\theta)w\}$$

θ=angle relative to plane of stage along which the film is pulled=90 degrees, implying $1-\cos\theta_{peel}=1-\cos 90°=1$
P=peel force measured from the PEEL FORCE TEST PROCEDURE
w=width of the film adherent
$E_f$=elastic modulus of film adherent
A=cross sectional area of the film adherent Peel Energy, $G_c$ of the body adhesive is then used to calculate $G_c/tE$, where t=thickness of the film adherent, and again, E=elastic modulus of the film adherent. It is also used to calculate tGE, described below.

"Peak Force at 20% Stretch" is determined by a test performed as follows. The PEAK FORCE-20% STRETCH TEST PROCEDURE is a measure of the force required to induced 20% strain in the sanitary napkin.

The apparatus necessary for the PEAK FORCE-20% STRETCH TEST PROCEDURE includes the following parts:
1. Instron Universal testing machine with load cell capable of measuring tensile forces up to 50 pounds.
2. Two inch wide upper and lower grips capable of gripping a typical napkin structure without slipping or tearing.

The PEAK FORCE-20% STRETCH TEST PROCEDURE may be performed using an apparatus similar to apparatus 60 described above with respect to the PEEL FORCE TEST PROCEDURE and FIG. 6. Release paper is removed from the body adhesive strips. Talcum powder is applied on the tacky portion to eliminate tack. Two points on opposite sides of the longitudinal centerline of the napkin that are covered with body adhesive are chosen as the test points. These points may be directly opposite the longitudinal centerline from each other or one may be further to the front or back than the other ("front-to-back positioning" is at the discretion of the tester). The points, however must be chosen so that each point can be centered across the width of its particular grip. The entire width of the grip will be contacting the sanitary napkin. Distance between the two points is measured and the gage length on the test machine is set to this value. Crosshead speed is set to 5.00 in/min and load limit is set to 45 lb for 50 lb load cell.

The sanitary napkin is stretched to a strain of 20% (i.e., the change in length between test points as a result of stretching via the test apparatus is 20% of the original length between test points. The Peak Force at 20% Stretch in grams is then read from the test apparatus. Five Replicates are tested to determine an average Peak Force at 20% Stretch for the sanitary napkin The product, $E_{nap}t$, is calculated using the formula below:

$$E_{nap}t = F/W\epsilon$$

$E_{nap}$=Effective elastic modulus of napkin
t=thickness of the sanitary napkin
F=Peak Force at 20% Stretch, measured by the PEAK FORCE-20% STRETCH TEST
W=width of the grip over which the specimen is held
ϵ=strain induced by test procedure=0.2

$E_{nap}t$ is multiplied by $G_c$, as calculated previously (from Peel Force, P that was measured previously in the PEEL FORCE TEST PROCEDURE) to determine $tG_cE_{nap}$, a measure of the sanitary napkin's ability to be peeled from the body with reduced pain.

EXAMPLES OF INVENTIVE SANITARY NAPKINS

Specific examples of inventive sanitary napkins are described below. Comparative examples are also provided.

All samples, except where noted used a 30 gsm multidenier nonwoven cover, unless where noted.

Inventive Sanitary Napkin, Ex. 1

A body-attachable sanitary napkin was made according to embodiments of the invention, in which the fluid-retaining portion was attached to the extensible barrier layer in a centrally disposed portion of a region of juxtaposition and unattached to said extensible barrier layer in other portions of the region of juxtaposition—similar to the sanitary napkin constructions shown in FIG. 5. The area of attachment measured 25 mm wide by 100 mm in length. The extensible barrier layer was highly extensible, ADC #9540002, and 80 gsm spunbond polyurethane/polyethylene nonwoven, commercially available from BBA Nonwovens of Peine, Germany. The body-contactable adhesive was selected for strong ability to stay in place, NS 548B, commercially available from National Starch Corporation of Bridgewater, N.J. The body-contactable adhesive was present in a basis weight of 76 gsm.

Inventive Sanitary Napkin, Ex. 2

A body-attachable sanitary napkin was made according to embodiments of the invention, with a construction similar to Ex. 1. The extensible barrier layer was moderately extensible, a 30 gsm thermobonded polypropylene commercially available from PGI, Inc of Dayton, N.J. The NS 548B body-contactable adhesive was present in a basis weight of 82 gsm.

Inventive Sanitary Napkin, Ex. 3

A body-attachable sanitary napkin was made according to embodiments of the invention, with a construction similar to Ex. 1. The extensible barrier layer was the highly extensible ADC #9540002. The body-contactable adhesive was selected for weaker ability to stay in place, Fuller 1407, commercially available from HB HB Fuller Co., of St. Paul, Minn. The body-contactable adhesive was present in a basis weight of 83 gsm.

Inventive Sanitary Napkin, Ex. 4

A body-attachable sanitary napkin was made according to embodiments of the invention, with a construction similar to Ex. 1, except that the fluid-retaining portion did not include portions that were unattached to the extensible barrier layer. The extensible barrier layer was the highly extensible ADC #9540002. The body-contactable adhesive was the "stronger" NS 548B adhesive. The body-contactable adhesive was present in a basis weight of 83 gsm.

Inventive Sanitary Napkin, Ex. 5

A body-attachable sanitary napkin was made according to embodiments of the invention, with a construction similar to Ex. 4. The extensible barrier layer was the highly extensible ADC #9540002. The body-contactable adhesive was the "weaker" Fuller 1407 adhesive. The body-contactable adhesive was present in a basis weight of 86 gsm.

Comparative Example, Sanitary Napkin, Comp. Ex 1

A body-attachable sanitary napkin was made with a construction similar to Ex. 4. The extensible barrier layer was chosen to have poor extensibility, a 25 gsm SMMS composite commercially available from BBA Nonwovens. The body-contactable adhesive was the "stronger" NS 548B adhesive.

Comparative Example, Sanitary Napkin, Comp. Ex. 2

A body-attachable sanitary napkin was made with a construction having a cover layer and barrier layer that extend beyond the fluid retaining layer, and the body-contactable adhesive present on the cover. Thus the sanitary napkin was similar to a conventional garment-attached sanitary napkin, but with body-contactable adhesive applied on the top side of the cover layer. The cover layer was an 80 gsm spunbond polyurethane/polyethylene nonwoven. The extensible barrier layer was the highly extensible ADC #9540002. The body-contactable adhesive was the "stronger" NS 548B adhesive.

Comparative Example, Sanitary Napkin, Comp. Ex. 3

A body-attachable sanitary napkin was made with a construction similar to Comp. Ex. 8. The extensible barrier layer was the moderately extensible 30 gsm thermobonded polypropylene. The body-contactable adhesive was the "stronger" NS 548B adhesive. The body-contactable adhesive was present in a basis weight of 83 gsm.

Comparative Example, Sanitary Napkin, Comp. Ex. 4

A body-attachable sanitary napkin was made according to embodiments of the invention, with a construction similar to Ex. 4. The extensible barrier layer was the poorly extensible SMMS. The body-contactable adhesive was the "weaker" Fuller 1407 adhesive. The body-contactable adhesive was present in a basis weight of 58 gsm.

The sanitary napkins suitable for use in the present invention and comparative samples were tested according to the test methods described in the "Test Procedures for Sanitary Articles" section above.

The peel force, P in grams was measured using the PEEL FORCE TEST PROCEDURE. Pliant #3471 0.7 mil white polypropylene film was used as the film adherent for the test. Peel Energy, $G_c$ was calculated using the formula described previously. The peel force in grams from the PEEL FORCE TEST PROCEDURE was converted to units of Newtons by multiplying by a geometric conversion factor of 0.0098 N/g. For this particular film adherent, the cross sectional area of the film adherent, A was 0.000018 m (width, w, was 0.01 m and thickness, t was 0.000018 m) and the elastic modulus of film adherent, $E_f$ was $383 \times 10^6$ N/m$^2$. $G_c$, thus calculated, had units of J/m$^2$ $G_c$/tE, the measure of stay in place, was then calculated using the thickness of the film adherent, t and Elastic Modulus, $E_f$ of the film adherent.

Peak Force at 20% Stretch measured using the PEAK FORCE-20% STRETCH TEST PROCEDURE. The Peak Force at 20% Stretch was converted to units of Newtons by multiplying by a geometric conversion factor of 0.0098 N/g. The width, W of the grip was 2 inches=5.08 cm. tGE, a measure of the sanitary napkin's ability to be peeled from the body with reduced pain, thus calculated, had units of N$^2$/m$^2$.

The results of which are set forth in Table 1 provided below.

TABLE 1

| Sample | Peel Force, F (g) | Peel energy, G (J/m2) | Peak Force @ 20% Stretch, F (g) CENTER | Peak Force @ 20% Stretch, F (g) END | Et (N/m) CENTER | Et (N/m) END | tGE (N$^2$/m$^2$) | G/Et |
|---|---|---|---|---|---|---|---|---|
| Ex. 1 | 96.6 | 94.7 | 471 | 302 | 454.3 | 291.3 | 2.8E+04 | 0.3252111 |
| Ex. 2 | 93.92 | 92.1 | 519 | 246 | 500.6 | 237.3 | 2.2E+04 | 0.3881591 |
| Ex. 3 | 137.18 | 134.6 | 544 | 333 | 524.7 | 321.2 | 4.3E+04 | 0.4189559 |
| Ex. 4 | 102.11 | 100.1 | 941 | 629 | 907.7 | 606.7 | 6.1E+04 | 0.1650555 |
| Ex. 5 | 166.43 | 163.3 | 1004 | 678 | 968.4 | 654.0 | 1.1E+05 | 0.2496979 |
| Comp Ex. 1 | 121.38 | 119.1 | 4369 | 3219 | 4214.2 | 3104.9 | 3.7E+05 | 0.0383441 |
| Comp Ex. 2 | 72.27 | 70.9 | 2641 | 1950 | 2547.4 | 1880.9 | 1.3E+05 | 0.0376741 |

TABLE 1-continued

| Sample | Peel Force, F (g) | Peel energy, G (J/m2) | Peak Force @ 20% Stretch, F (g) CENTER | Peak Force @ 20% Stretch, F (g) END | Et (N/m) CENTER | Et (N/m) END | tGE (N²/m²) | G/Et |
|---|---|---|---|---|---|---|---|---|
| Comp Ex. 3 | 79.19 | 77.7 | 2698 | 1940 | 2602.4 | 1871.3 | 1.5E+05 | 0.0414963 |
| Comp Ex. 4 | 18.32 | 18.0 | 4632 | 3221 | 4467.9 | 3106.9 | 5.6E+04 | 0.0057794 |

Figure 7:
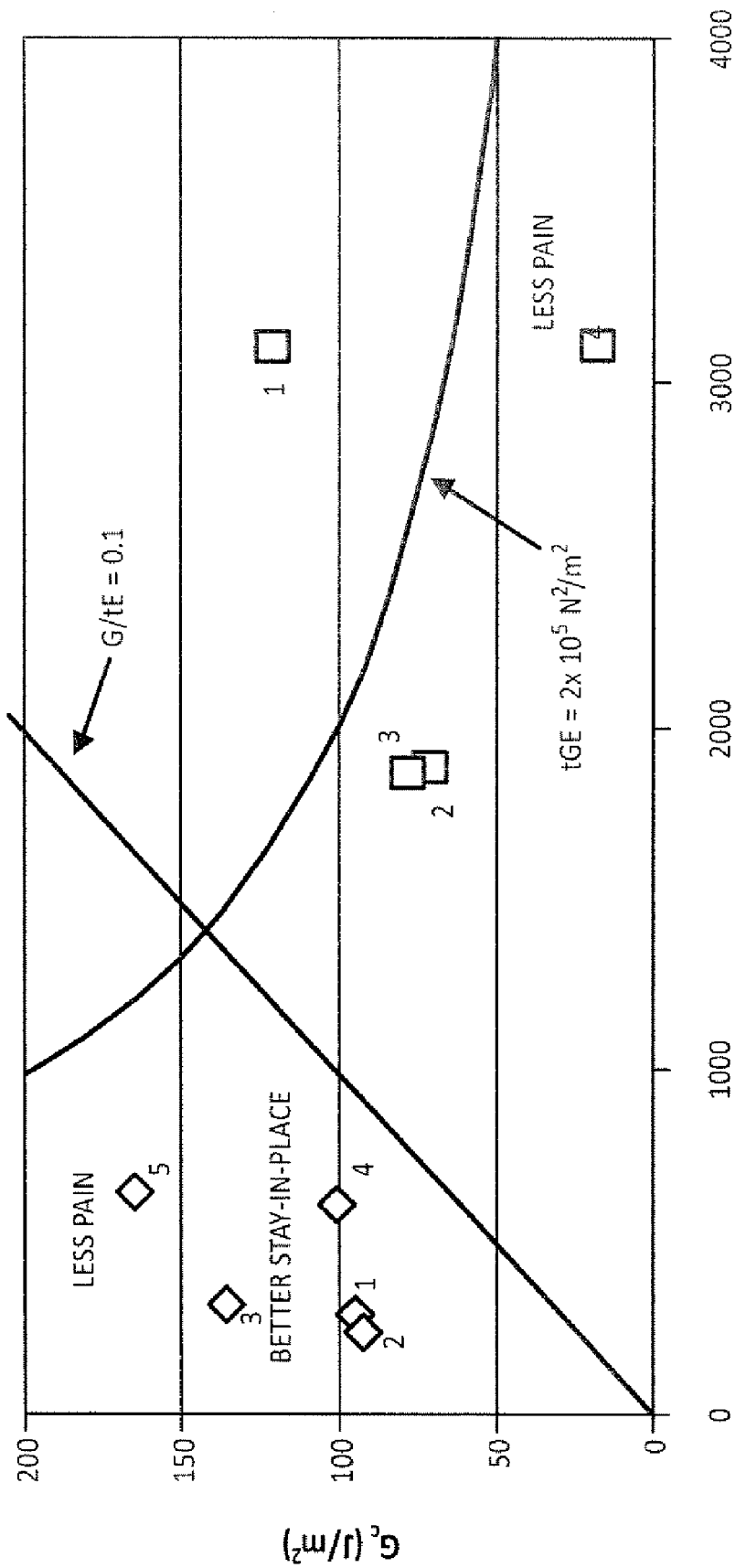
FIG. 7 is a graphical depiction of stay-in-place and removal pain for inventive sanitary napkins as well as comparative examples.

The results are shown graphically in FIG. 7. The particular example is matched with the data point in the Figure. Points above the line, G/tE=0.1 indicate high stay-in-place. Points below the curve, tGE=2×10⁵ N²/m² indicate lower removal pain. The points in the upper left quadrant (where Examples 1-5 fall) combine both high stay-in-place as well as lower removal pain.

In view of the above absorbent articles and results of test procedures provided herein, it can be seen that by sanitary napkins of the present invention remain securely attached to the body during use, move with the body during use, yet at the same time enable the user to selectively remove the napkin in a pain free manner.

Applications of the sanitary napkin according to the present invention for sanitary and other health care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

I claim:

1. A body-attachable sanitary napkin, comprising:
    an extensible barrier layer having a first portion and a second portion, said second portion having a body-attachable adhesive arranged thereon; and
    a fluid-retaining assembly arranged in overlapping relationship to said first portion of said barrier layer thereby defining an area of juxtaposition between said fluid-retaining assembly and said barrier layer,
    wherein said fluid-retaining assembly is secured to said barrier layer along a selected portion of said area of juxtaposition; and
    wherein a total area of the fluid retaining assembly is about 10% to about 90% of a total area of the extensible barrier layer;
    wherein the selected portion of the area of juxtaposition has an area fraction that is from about 30% to about 70% of the area of juxtaposition; and
    said sanitary napkin satisfies the following:

$$G/tE > 0.1 \text{ and } tGE < 2 \times 10^5 \text{ N}^2/\text{m}^2.$$

2. The body-attachable sanitary napkin of claim 1, wherein the overlapping relationship between said first portion of said barrier layer and said fluid-retaining assembly further defines a peripheral region of juxtaposition, and wherein at least about 50% of the peripheral region of juxtaposition is not secured to the barrier layer.

3. The body-attachable sanitary napkin of claim 1, wherein the overlapping relationship between said first portion of said barrier layer and said fluid-retaining assembly further defines a segment of unattachment and a segment of attachment, and wherein the length of the segment of unattachment is greater than about 15% of that of the length of the segments of attachment.

4. The body-attachable sanitary napkin of claim 1, further comprising an additional barrier layer positioned intermediate the fluid-retaining assembly and the extensible barrier layer.

5. The body-attachable sanitary napkin of claim 4, wherein the additional barrier layer does not extend beyond the area of juxtaposition.

6. The body-attachable sanitary napkin of claim 4, wherein the additional barrier layer is free of body-contactable adhesive.

7. The body-attachable sanitary napkin of claim 1, wherein said extensible barrier further comprises a third portion having a body-contactable surface, wherein the third portion is free of body-contactable adhesive.

* * * * *